United States Patent
Kubota et al.

(10) Patent No.: US 10,390,719 B2
(45) Date of Patent: Aug. 27, 2019

(54) PATCH-TYPE ADHESIVE SENSOR

(71) Applicants: SHINKO ELECTRIC INDUSTRIES CO., LTD., Nagano (JP); NIHON KOHDEN CORPORATION, Tokyo (JP)

(72) Inventors: Kazuyuki Kubota, Nagano (JP); Norihito Konno, Tokyo (JP)

(73) Assignees: SHINKO ELECTRIC INDUSTRIES CO., LTD., Nagano (JP); NIHON KOHDEN CORPORATION, Tokyo (JP)

( * ) Notice: Subject to any disclaimer, the term of this patent is extended or adjusted under 35 U.S.C. 154(b) by 365 days.

(21) Appl. No.: 15/163,865

(22) Filed: May 25, 2016

(65) Prior Publication Data
US 2016/0360991 A1 Dec. 15, 2016

(30) Foreign Application Priority Data
Jun. 9, 2015 (JP) .................................. 2015-116740

(51) Int. Cl.
*A61B 5/0408* (2006.01)
*A61B 5/021* (2006.01)
(Continued)

(52) U.S. Cl.
CPC ............ *A61B 5/04087* (2013.01); *A61B 5/01* (2013.01); *A61B 5/021* (2013.01); *H01M 2/1022* (2013.01);
(Continued)

(58) Field of Classification Search
USPC ....................................................... 600/392
See application file for complete search history.

(56) References Cited

U.S. PATENT DOCUMENTS 4,105,830 A * 8/1978 Kordesch ............... H01M 4/00
429/405
4,591,539 A * 5/1986 Oltman ................. H01M 12/06
29/623.1
(Continued)

FOREIGN PATENT DOCUMENTS

JP 2012-141186 7/2012

OTHER PUBLICATIONS

"Technical/OEM primary systems", Duracell, copyright 2004,<https://d2ei442zrkqy2u.cloudfront.net/wp-content/uploads/2016/03/Zinc-Air-Tech-Bulletin.pdf>.*
(Continued)

*Primary Examiner* — Christopher Koharski
*Assistant Examiner* — James Moss
(74) *Attorney, Agent, or Firm* — IPUSA, PLLC

(57) ABSTRACT

A patch-type module includes a substrate provided with one surface and another surface that is a sticky surface; an air cell mounted to the substrate; a seal that blocks air from entering the air cell whose first surface is attached to the air cell; an electronic component mounted on the substrate; and a protection sheet that is attached to the sticky surface of the substrate through an adhesion layer, wherein a second surface of the seal is attached to the protection sheet through the adhesion layer, wherein when the protection sheet is peeled, the adhesion layer and the seal are peeled together to expose the sticky surface of the substrate and start introduction of air inside the air cell so that electric power is capable of being power supplied to the electronic component from the air cell.

6 Claims, 9 Drawing Sheets

(51) Int. Cl.
 *A61B 5/01* (2006.01)
 *H01M 2/10* (2006.01)
 *H01M 12/06* (2006.01)

(52) U.S. Cl.
 CPC ..... *H01M 12/06* (2013.01); *A61B 2560/0214* (2013.01); *A61B 2562/06* (2013.01)

(56) References Cited

U.S. PATENT DOCUMENTS

| | | | | |
|---|---|---|---|---|
| 5,662,925 | A * | 9/1997 | Ebert | A61K 9/703 424/447 |
| 6,329,095 | B1 * | 12/2001 | Farnworth | H01M 8/04082 429/163 |
| 2008/0146958 | A1 * | 6/2008 | Guillory | A61B 5/0476 600/544 |
| 2013/0225967 | A1 | 8/2013 | Esposito | |
| 2014/0288381 | A1 * | 9/2014 | Faarbaek | A61B 5/0002 600/300 |

OTHER PUBLICATIONS

Office Action dated Aug. 7, 2018 issued with respect to the basic Japanese Patent Application No. 2015-116740.

* cited by examiner

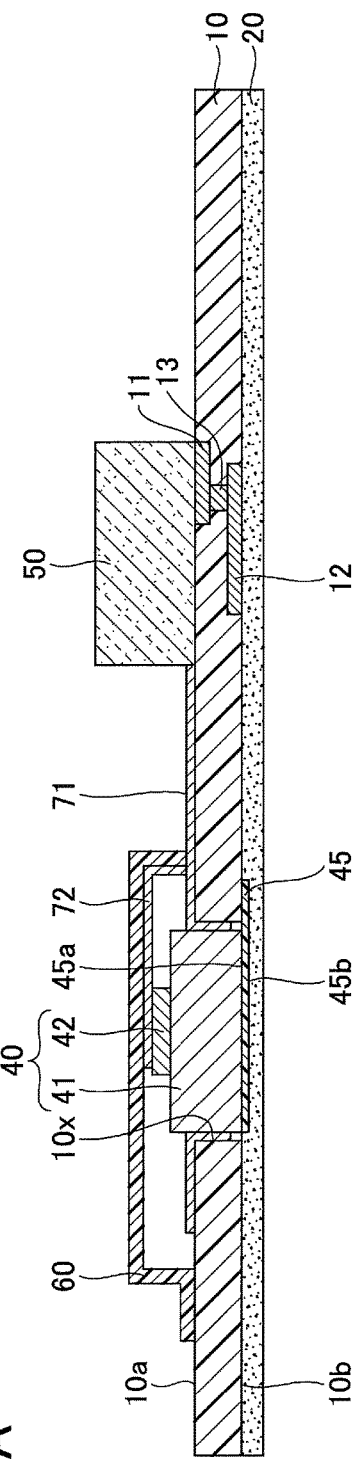
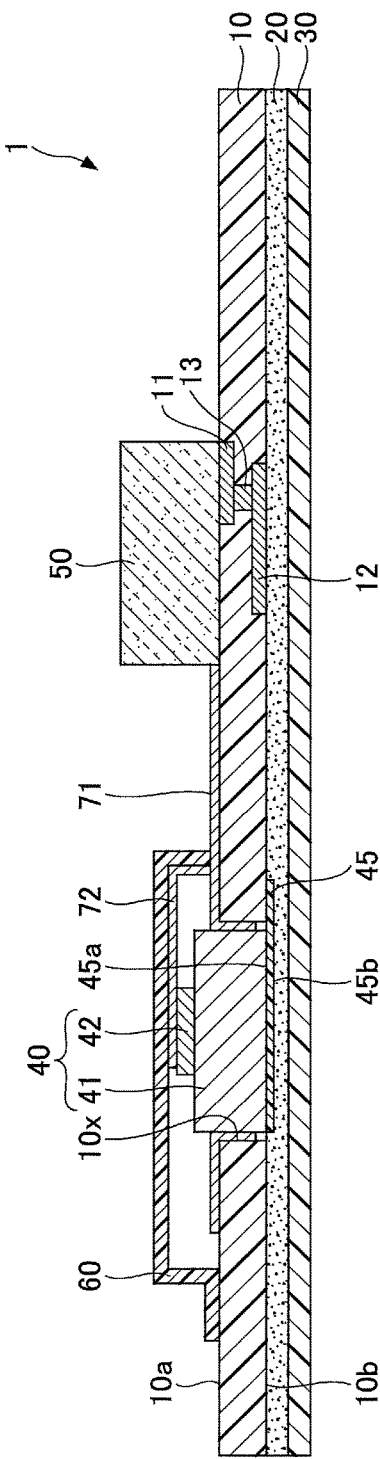
FIG.3A
FIG.3B

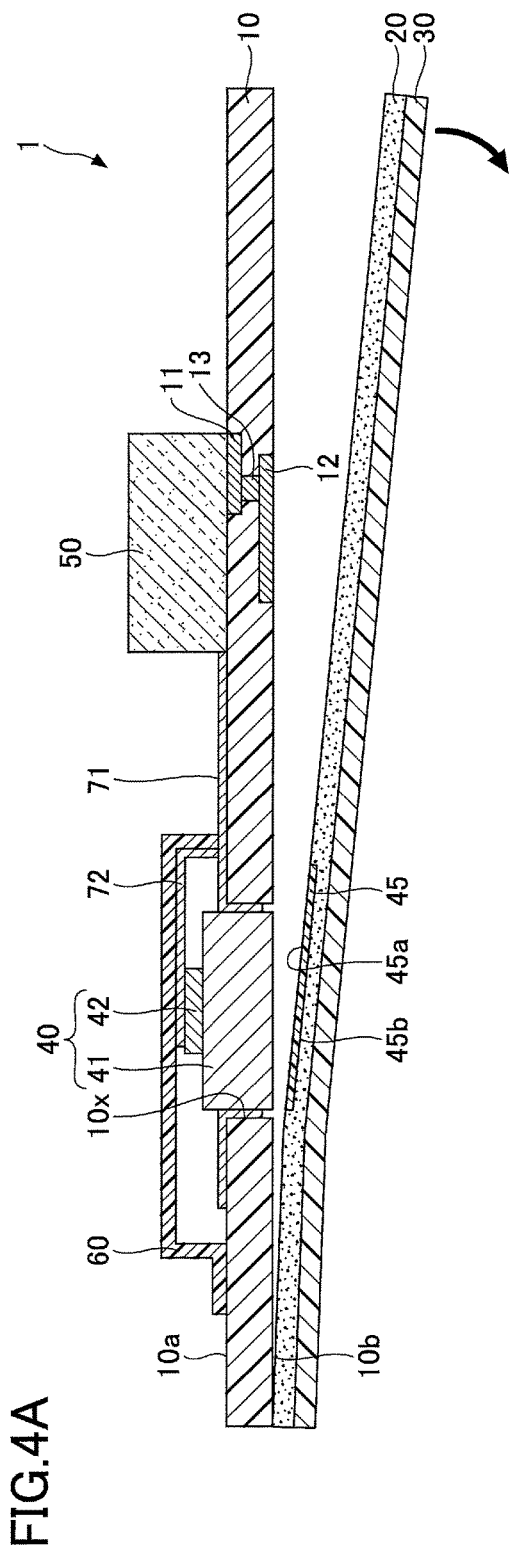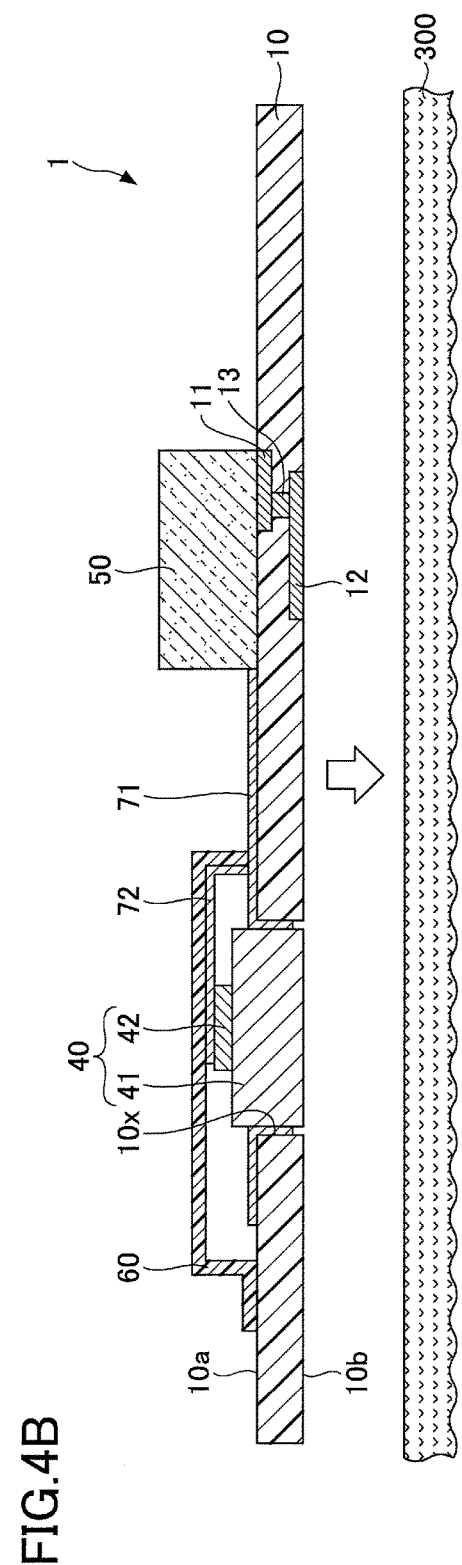

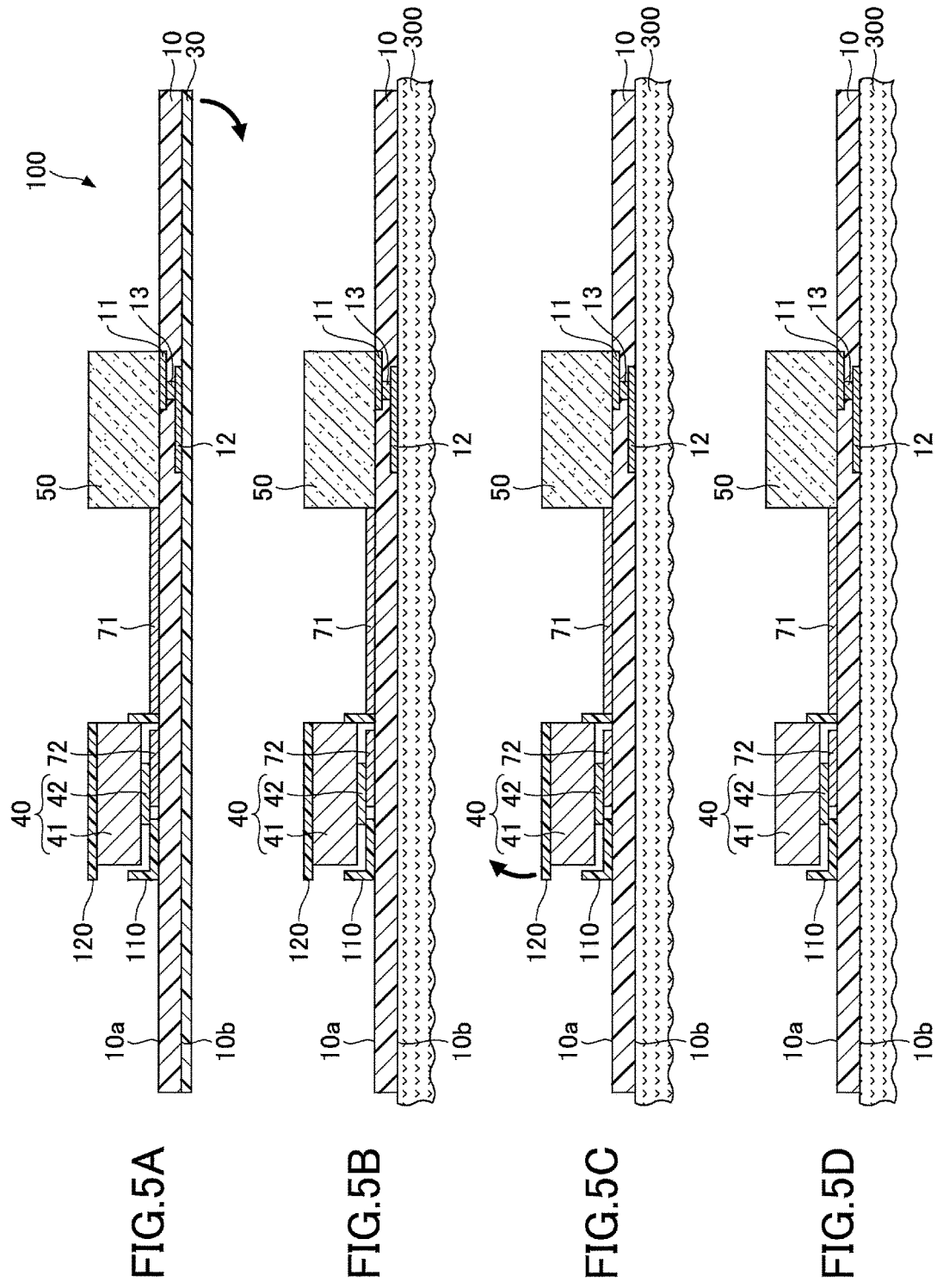

PATCH-TYPE ADHESIVE SENSOR

CROSS-REFERENCE TO RELATED APPLICATIONS

The present application is based on and claims the benefit of priority of Japanese Priority Application No. 2015-116740 filed on Jun. 9, 2015, the entire contents of which are hereby incorporated by reference.

FIELD

The present invention relates to a patch-type module.

BACKGROUND

Conventionally, a medical patch-type module is known, such as a polymer substrate or the like, capable of being stuck on various targets such as the skin of a human or the like (see Patent Document 1, for example). A protection sheet is attached on a sticky surface in a patch-type module, and the sticky surface can be stuck on a target by peeling the protection sheet and exposing the sticky surface.

An electronic component and a cell may be mounted on such a patch-type module, and the electronic component may be operated by electric power supplied from the cell. A seal that blocks a function of the cell is attached, and the cell is insulated until it is used.

When using the patch-type module in which the cell is mounted, an operation to peel the seal of the cell so that the cell is caused to function, and an operation to peel the protection sheet and expose the sticky surface for sticking the patch-type module on the target, are necessary, and this is troublesome (as will be explained as a comparative example, for example).

Patent Document 1: Japanese Laid-open Patent Publication No. 2012-141186

SUMMARY

The present invention is made in light of the above problems, and provides a patch-type module capable of starting an operation of a cell and exposing a sticky surface by a single peeling operation.

According to an embodiment, there is provided a patch-type module including a substrate provided with one surface and another surface that is opposite to the one surface, the other surface being a sticky surface; an air cell mounted to the substrate; a seal that blocks air from entering the air cell, the seal having a first surface that is attached to the air cell; an electronic component mounted on the substrate and configured to be operated by power supplied from the air cell; and a protection sheet that is attached to the sticky surface of the substrate through an adhesion layer, wherein a second surface of the seal, that is opposite to the first surface, is attached to the protection sheet through the adhesion layer, wherein when the protection sheet is peeled, the adhesion layer and the seal are peeled together to expose the sticky surface of the substrate and start introduction of air inside the air cell so that electric power is capable of being power supplied to the electronic component from the air cell.

BRIEF DESCRIPTION OF DRAWINGS

Other objects, features and advantages of the present invention will become more apparent from the following detailed description when read in conjunction with the accompanying drawings.

FIG. 3A and FIG. 3B are cross-sectional views (No. 2) illustrating an example of manufacturing steps of the patch-type module of the first embodiment;

FIG. 4A and FIG. 4B are cross-sectional views for explaining how to use the patch-type module of the first embodiment;

FIG. 5A to FIG. 5D are cross-sectional views for explaining how to use a patch-type module of a comparative example;

DESCRIPTION OF EMBODIMENTS

The invention will be described herein with reference to illustrative embodiments. Those skilled in the art will recognize that many alternative embodiments can be accomplished using the teachings of the present invention and that the invention is not limited to the embodiments illustrated for explanatory purposes.

First Embodiment (Structure of Patch-Type Module of First Embodiment)

Figure 1A:
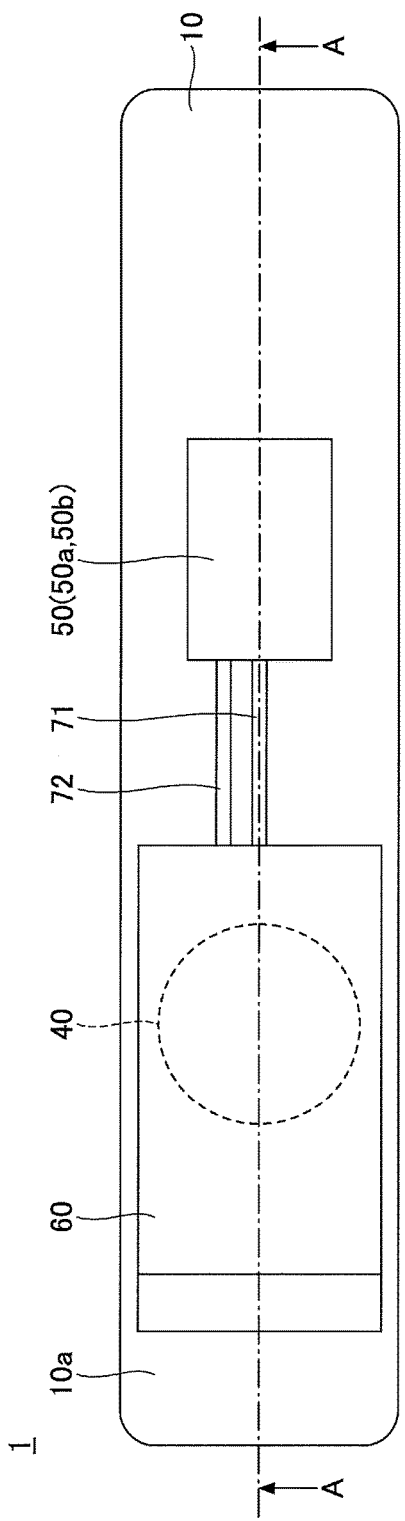
FIG. 1A and FIG. 1B are views illustrating an example of a patch-type module of a first embodiment.
Figure 1B:
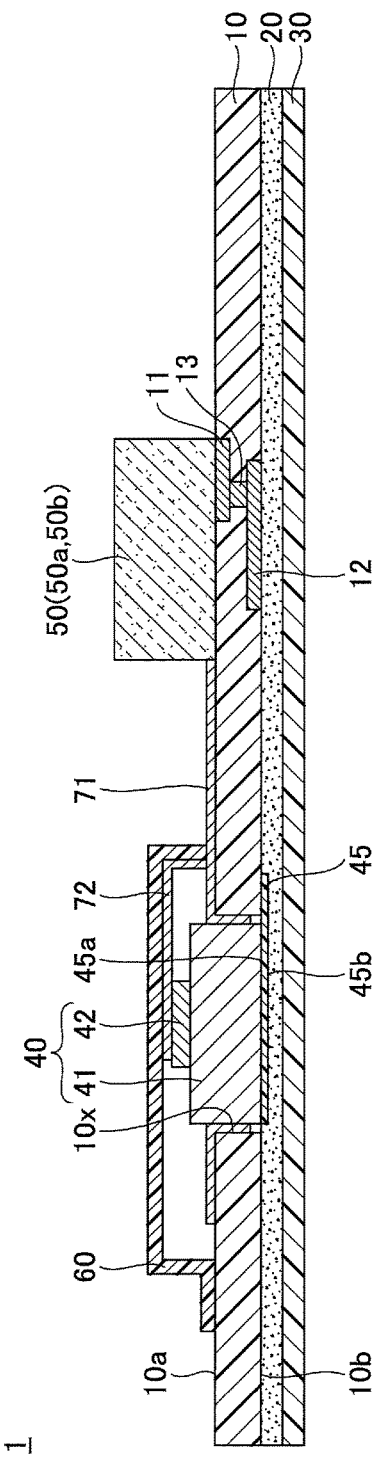

First, a structure of a patch-type module of the first embodiment is explained. FIG. 1A and FIG. 1B are views illustrating an example of a patch-type module 1 of the first embodiment, wherein FIG. 1A is a plan view and FIG. 1B is a cross-sectional view taken along an A-A line of FIG. 1A.

With reference to FIG. 1A and FIG. 1B, the patch-type module 1 includes a substrate 10, an adhesion layer 20, a protection sheet 30, an air cell 40, an electronic component 50, a wiring forming portion 60 and wirings 71 and 72.

The patch-type module 1 is an apparatus that is stuck on a target and obtains predetermined data from the target. For example, as will be explained below, a memory may be mounted on the patch-type module 1 and the obtained data may be stored in the memory, or a radio transmitter may be mounted on the patch-type module 1 and the obtained data may be transmitted by radio communication. The target may be a human body, for example, and the patch-type module 1 may monitor predetermined data of the human body. In such a case, a target to be monitored may be blood pressure, pulse, electrocardiograph, body temperature or the like.

In this embodiment, an electronic component 50 side of the patch-type module 1 is referred to as an upper side or one side, and a protection sheet 30 side of the patch-type module 1 is referred to as a lower side or the other side. Further, a surface of each component at the electronic component 50 side is referred to as one surface or an upper surface, and a surface at the protection sheet 30 side is referred to as the other surface or a lower surface. However, the patch-type module 1 may be used in an opposite direction or may be used at an arbitrary angle. Further, in this embodiment, "in a plan view" means that an object is seen in a direction that is normal to one surface 10a of the substrate 10, and a "plan shape" means a shape of an object seen in the direction that is normal to the one surface 10a of the substrate 10.

The substrate 10 is a base for mounting the air cell 40, the electronic component 50 or the like, and is an elongated adhesive (sticky) tape with flexibility and stretchability. The substrate 10 is provided with the one surface 10a, and the other surface 10b that is opposite to the one surface 10a.

An inner electrode 11 is formed at the one surface 10a side of the substrate 10, and the inner electrode 11 is electrically connected to the electronic component 50. Further, an outer electrode 12 is formed at the other surface 10b side of the substrate 10. The outer electrode 12 is an electrode for sensing. The outer electrode 12 contacts a target by being exposed from the other surface 10b of the substrate 10, when the adhesion layer 20 and the protection sheet 30 are peeled from the other surface 10b of the substrate 10 and the other surface 10b of the substrate 10 is stuck on the target (see FIG. 4B which will be explained later). The inner electrode 11 and the outer electrode 12 are electrically connected with each other through a via wiring 13, and predetermined data from the target is input to the electronic component 50 through the outer electrode 12, the via wiring 13 and the inner electrode 11.

For the material of the substrate 10, polyolefin, polypropylene, polyester, polyethylene, polyurethane or the like may be used, for example. The other surface 10b of the substrate 10 is configured to be a sticky surface (not illustrated in the drawings). The sticky surface may be formed by an acrylic-based adhesive agent, a rubber-based adhesive agent, a silicone-based adhesive agent or the like, for example. The size of the substrate 10 (in a plan view) may be arbitrarily determined, and, for example, may be about 10 to 30 mm in a short direction and about 80 to 120 mm in a longitudinal direction. The thickness of the substrate 10 may be about 25 to 75 µm, for example.

The adhesion layer 20 is attached to the other surface 10b of the substrate 10 to adhere the protection sheet 30 to the substrate 10. For the material of the adhesion layer 20, an acrylic-based adhesive agent, a rubber-based adhesive agent, a silicone-based adhesive agent or the like may be used, for example. The thickness of the adhesion layer 20 may be about 5 to 15 µm, for example.

The protection sheet 30 is attached to the other surface 10b of the substrate 10, which is a sticky surface, through the adhesion layer 20. For the material of the protection sheet 30, silicone-based resin, fluorine-based resin, a paper base or the like may be used, for example. The thickness of the protection sheet 30 may be about 25 to 75 µm, for example.

The air cell 40 is mounted to (or mounted in) the substrate 10. More specifically, the substrate 10 is provided with a cell housing portion 10x that penetrates from the one surface 10a to the other surface 10b, and an upper surface of the adhesion layer 20 is exposed at a bottom portion of the cell housing portion 10x. A first surface 45a of a seal 45 is attached to a back surface side of the air cell 40. The air cell 40 is housed in the cell housing portion 10x such that a second surface 45b of the seal 45, which is opposite to the first surface 45a, exposes at the other surface 10b side of the substrate 10. The second surface 45b of the seal 45 is attached to the adhesion layer 20 by being in contact with an upper surface of the adhesion layer 20 that is exposed at the bottom portion of the cell housing portion 10x. In other words, the second surface 45b of the seal 45 is attached to the protection sheet 30 through the adhesion layer 20. Here, the seal 45 has a function to block air from entering inside the air cell 40.

The air cell 40 is a cell that uses oxygen in the air as an active material of a positive electrode, and uses a metal as an active material of a negative electrode. When the seal 45 attached to the back surface side of the air cell 40 is peeled and the air is introduced into the inside, the air cell 40 is caused to function as a cell. Thus, under a status illustrated in FIG. 1A and FIG. 1B, as the seal 45 is attached at the back surface side, the air cell 40 is not functioning as a cell.

The air cell 40 includes a main body 41 that is a positive electrode, and a negative electrode 42 that is protruded from the main body 41 (the main body 41 and the negative electrode 42 are insulated). A side surface of the main body 41, that is the positive electrode, contacts an one end side of the wiring 71 that extends from the one surface 10a of the substrate 10 to an inner sidewall surface of the cell housing portion 10x so that the main body 41 and the wiring 71 are electrically connected. The other end side of the wiring 71 is electrically connected to the electronic component 50.

The negative electrode 42 contacts one end side of the wiring 72 that is provided at an inner sidewall surface of the wiring forming portion 60, and the negative electrode 42 and the wiring 72 are electrically connected. The wiring 72 extends from the inner sidewall surface of the wiring forming portion 60 to the one surface 10a of the substrate 10 and the other end side of the wiring 72 is electrically connected with the electronic component 50. The wiring forming portion 60 may be formed by a flexible printed substrate, for example.

For the material of the wirings 71 and 72, copper (Cu) or the like may be used, for example. The thickness of each of the wirings 71 and 72 may be about 10 to 20 µm, for example. In accordance with necessity, an arbitrarily patterned wiring (an electrode for mounting the electronic component 50 or the like, for example) may be provided in addition to the wirings 71 and 72. Further, wirings may be provided inside the substrate 10. In such a case, arbitrarily selected wirings may be connected through via wirings to form a multi-layered wiring.

The electronic component 50 is mounted on the one surface 10a of the substrate 10. The electronic component 50 includes a sensor 50a (an acceleration sensor, a temperature sensor or the like) that obtains predetermined data from the target, a semiconductor device 50b or the like, for example. Further, the electronic component 50 may obtain data regarding pulse, electrocardiograph or the like, for example, by being electrically connected to a specific sensor (not illustrated in the drawings) that contacts the target and obtains predetermined data. The semiconductor device 50b is a semiconductor memory, which is a memory unit that stores the predetermined data obtained by the sensor 50a, a radio transmitter that sends the predetermined data to an external device by radio communication, a CPU (Central Processing Unit) or the like, for example.

As described above, the electronic component 50 is connected to the air cell 40 via the wirings 71 and 72. When the seal 45 attached at the back surface side of the air cell 40 is peeled and the air cell 40 is caused to function as a cell, electric power (voltage=1.25v, for example) is supplied to the electronic component 50 from the air cell 40 through the wirings 71 and 72 and the electronic component 50 is capable of being operated.

For the patch-type module 1, when the protection sheet 30 is peeled, the adhesion layer 20 and the seal 45 are peeled together. With this configuration, the other surface 10b of the substrate 10, which is the sticky surface, is exposed, and introduction of air inside the air cell 40 is started and electric power can be supplied from the air cell 40 to the electronic component 50.

(Method of Manufacturing Patch-Type Module of First Embodiment)

Figure 2:
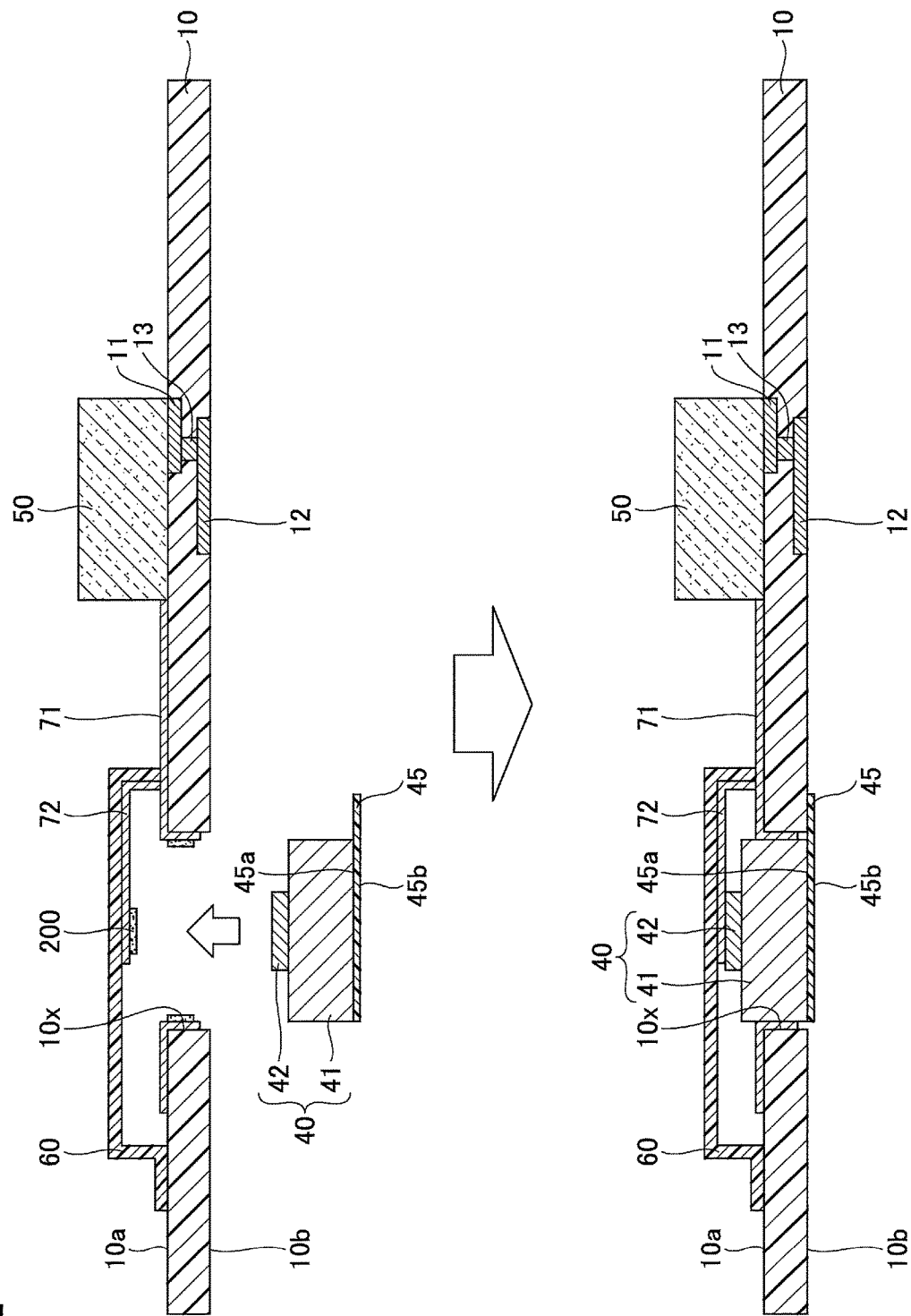
FIG. 2 is a cross-sectional view (No. 1) illustrating an example of a manufacturing step of the patch-type module of the first embodiment.

Next, a method of manufacturing the patch-type module 1 of the first embodiment is described. FIG. 2, FIG. 3A and FIG. 3B are cross-sectional views illustrating an example of manufacturing steps of the patch-type module 1 of the first embodiment.

First, in a step illustrated in FIG. 2, the cell housing portion 10x that penetrates from the one surface 10a to the other surface 10b of the substrate 10 is formed in the substrate 10 by press working or the like. Then, the wiring forming portion 60 is fixed to the one surface 10a of the substrate 10. Then, after forming the wirings 71 and 72 at predetermined positions, respectively, by known plating, sputtering or the like, the electronic component 50 is mounted on the one surface 10a of the substrate 10 by reflowing or the like. Further, a conductive adhesive agent 200 such as a silver paste or the like is coated at predetermined positions of the wirings 71 and 72, respectively, in the cell housing portion 10x.

Next, the air cell 40, in which the first surface 45a of the seal 45 is attached to the back surface side, is housed in the cell housing portion 10x from the other surface 10b side of the substrate 10 while the negative electrode 42 being at an upper side, and the conductive adhesive agent 200 is cured. With this, the main body 41 (positive electrode) of the air cell 40 is electrically connected to the wiring 71 through the conductive adhesive agent 200, and the negative electrode 42 of the air cell 40 is electrically connected to the wiring 72 through the conductive adhesive agent 200. Further, a portion of the first surface 45a of the seal 45 that is protruded from the main body 41 adheres to the other surface 10b of the substrate 10. This means that the air cell 40 in which the seal 45 is attached at the back surface side, is housed in the cell housing portion 10x such that the second surface 45b of the seal 45 is exposed at the other surface 10b side of the substrate 10.

Next, in a step illustrated in FIG. 3A, the adhesion layer 20 is formed on the other surface 10b of the substrate 10 such as to cover the seal 45. The adhesion layer 20 may be formed by laminating an adhesive agent film, for example. Alternatively, the adhesion layer 20 may be formed by coating a liquid or paste adhesive agent.

Next, in a step illustrated in FIG. 3B, the protection sheet 30 is attached at the entirety of a lower surface side of the adhesion layer 20. With this, the protection sheet 30 is attached to the other surface 10b of the substrate 10 and the second surface 45b of the seal 45 through the adhesion layer 20.

Here, materials or the like of the adhesion layer 20, the protection sheet 30 and the seal 45 are selected such that the adhesion strength between the adhesion layer 20 and the protection sheet 30 and the adhesion strength between the adhesion layer 20 and the seal 45 become greater than the adhesion strength between the seal 45 and the back surface of the main body 41 of the air cell 40 and the adhesion strength of the seal 45 and the other surface 10b of the substrate 10. Further, materials or the like of the adhesion layer 20 and the protection sheet 30 are selected such that the adhesion strength between the adhesion layer 20 and the protection sheet 30 becomes greater than the adhesion strength between the adhesion layer 20 and the other surface 10b of the substrate 10.

With the above steps, the patch-type module 1 is completed. Here, steps to manufacture a single patch-type module 1 are described here. However, alternatively, a plurality of the patch-type modules 1 may be formed by using the substrate 10 in which a plurality or areas corresponding to the plurality of patch-type modules 1, respectively, are aligned in a matrix form, and each of the patch-type modules 1 may be separated by press working or the like to obtain a plurality of the single patch-type modules 1.

FIG. 4A and FIG. 4B are cross-sectional views for explaining how to use the patch-type module 1 of the first embodiment. When using the patch-type module 1, first, as illustrated in FIG. 4A, the protection sheet 30 is peeled in a direction of an arrow.

As described above, the adhesion strength between the adhesion layer 20 and the protection sheet 30 and the adhesion strength between the adhesion layer 20 and the seal 45 are greater than the adhesion strength between the seal 45 and the back surface of the main body 41 of the air cell 40 and the adhesion strength between the seal 45 and the other surface 10b of the substrate 10. Further, the adhesion strength between the adhesion layer 20 and the protection sheet 30 is greater than the adhesion strength between the adhesion layer 20 and the other surface 10b of the substrate 10.

Thus, when the protection sheet 30 is peeled in the direction of the arrow, the adhesion layer 20 is peeled from an interface with the other surface 10b of the substrate 10 together with the protection sheet 30. Further, the seal 45 is peeled from interfaces with the back surface of the main body 41 of the air cell 40 and the other surface 10b of the substrate 10 together with the protection sheet 30 and the adhesion layer 20. With this, introduction of air inside the air cell 40 is started and it is possible to supply electric power from the air cell 40 to the electronic component 50.

Next, as illustrated in FIG. 4B, the other surface 10b of the substrate 10 that has stickiness is stuck on a target 300. The target 300 is a human body, for example, and the patch-type module 1 is stuck to a surface of the skin of the human body. For example, when a target to be monitored is pulse, the patch-type module 1 is attached to an arm. Alternatively, when the target to be monitored is electrocardiograph, the patch-type module 1 is attached to a breast. With this, predetermined data of the human body can be monitored using the patch-type module 1.

Here, with reference to a comparative example, specific effects of the patch-type module 1 are explained. FIG. 5A to FIG. 5D are cross-sectional views for explaining how to use a patch-type module 100 of a comparative example. Different from the patch-type module 1, the protection sheet 30 is directly attached to the other surface 10b of the substrate 10 without the adhesion layer 20 in the patch-type module 100. Further, a cell holder 110 is provided at the one surface 10a of the substrate 10, and the air cell 40 is placed in the cell holder 110 such that the negative electrode 42 faces the one surface 10a side of the substrate 10. A seal 120 is attached to a back surface side of the air cell 40. The air cell 40 does not function before the seal 120 is peeled.

When using the patch-type module 100, first, as illustrated in FIG. 5A, the protection sheet 30 is peeled in a direction of an arrow to expose the other surface 10b of the substrate 10, which is a sticky surface. Next, as illustrated in FIG. 5B, the other surface 10b of the substrate 10, which is the sticky surface, is stuck on the target 300. Then, as illustrated in FIG. 5C, the seal 120 is peeled in a direction of an arrow so that the air cell 40 is caused to function. With this, the patch-type module 100 becomes a state as illustrated in FIG. 5D and the air cell 40 starts its operation.

As such, when using the patch-type module 100, two operations are necessary including an operation of peeling the protection sheet 30 to expose the other surface 10b of the substrate 10 (sticky surface) and an operation of peeling the seal 120 so that the air cell 40 is caused to function, and this is troublesome.

On the other hand, according to the patch-type module 1 of the first embodiment, as illustrated in FIG. 4A and FIG. 4B, the protection sheet 30 and the seal 45 are peeled at the same time by a single peeling operation, and usability is improved. In other words, as it is possible to start the operation of the air cell 40 and to expose the other surface 10b of the substrate 10, which is the sticky surface, by a single operation, usability is improved.

Further, as the through hole provided in the substrate 10 is used as the cell housing portion 10x and the air cell 40 is housed in the cell housing portion 10x, it is unnecessary to use the cell holder 110. Here, the patch-type modules 1 and 100 may be disposable modules, respectively. In such a case, using of the cell holder 110 increases the cost of the module and also is not eco-friendly. As the cell holder 110 is not used in the patch-type module 1, the module can be obtained by a low cost and also is eco-friendly.

Second Embodiment

In a second embodiment, an example of the patch-type module is described in which the shape or the like of the protection sheet is different from that of the first embodiment. It is to be noted that, in the explanation of the second embodiment, the same components may be given the same reference numerals, and explanations may not be repeated.
(Structure of Patch-Type Module of Second Embodiment)

Figure 6A:
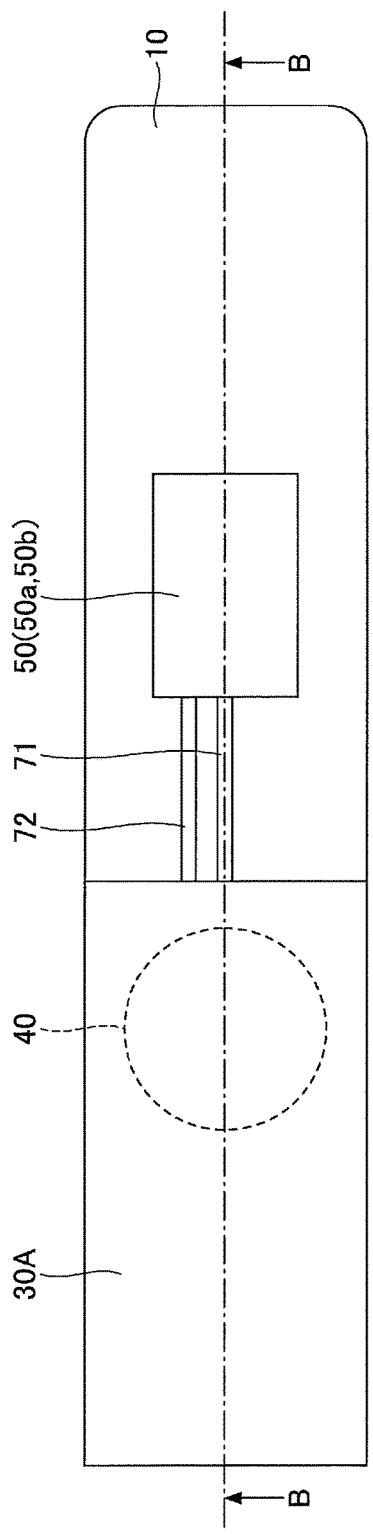
FIG. 6A and FIG. 6B are views illustrating an example of a patch-type module of a second embodiment.
Figure 6B:
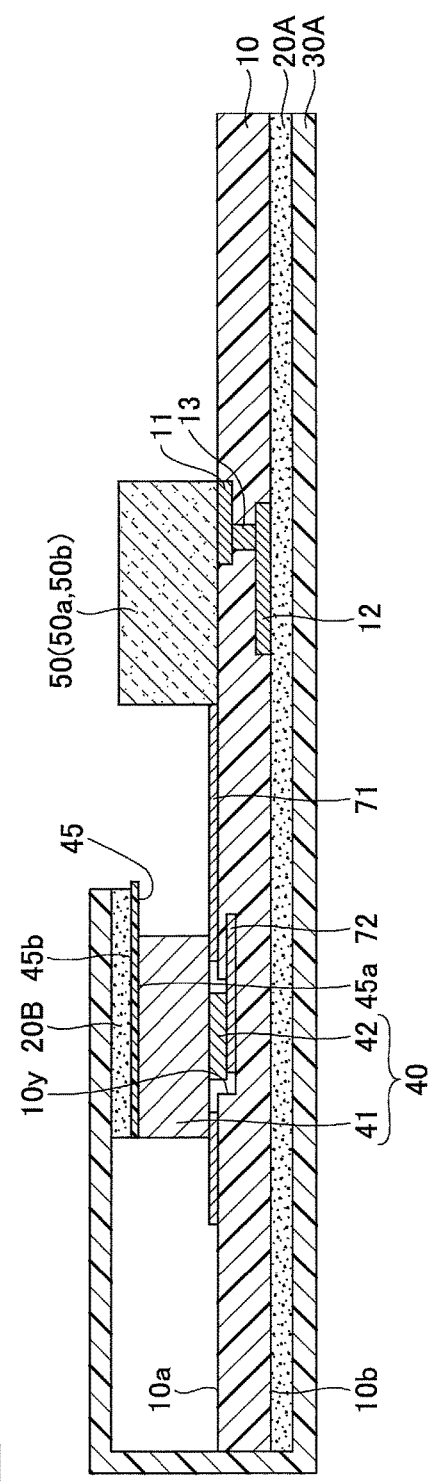

First, a structure of the patch-type module of the second embodiment is described. FIG. 6A and FIG. 6B are views illustrating an example of a patch-type module 1A of the second embodiment, wherein FIG. 6A is a plan view and FIG. 6B is a cross-sectional view of FIG. 6A taken along a B-B line of FIG. 6A.

With reference to FIG. 6A and FIG. 6B, a concave portion 10y is provided at the one surface 10a of the substrate 10 and the wiring 72 is formed in the concave portion 10y in the patch-type module 1A of the second embodiment. Further, the air cell 40 is placed on the one surface 10a of the substrate 10 under a status that is upside down from that of the patch-type module 1. More specifically, the air cell 40 is directly mounted on the one surface 10a side of the substrate 10 such that its negative electrode 42 is housed in the concave portion 10y provided in the substrate 10 and the first surface 45a of the seal 45 faces the one surface 10a of the substrate 10 while interposing the air cell 40 therebetween.

A surface of the main body 41 at the negative electrode 42 side, which becomes a positive electrode of the air cell 40 contacts one end side of the wiring 71 that is formed on the one surface 10a of the substrate 10, and the surface of the main body 41 and the wiring 71 are electrically connected with each other. Another end side of the wiring 71 is electrically connected with the electronic component 50.

The negative electrode 42 contacts one end side of the wiring 72 provided in the concave portion 10y, and the negative electrode 42 and the wiring 72 are electrically connected with each other. The wiring 72 extends from the concave portion 10y toward the one surface 10a of the substrate 10 through a via wiring (not illustrated in the drawings), for example, and another end side of the wiring 72 is electrically connected with the electronic component 50.

An adhesion layer 20A is attached on the other surface 10b of the substrate 10 and an adhesion layer 20B is attached on the second surface 45b of the seal 45. The material and the thickness of each of the adhesion layers 20A and 20B may be the same as those of the adhesion layer 20, for example.

The protection sheet 30A is formed to be longer than each of the substrate 10 and the adhesion layer 20A in a longitudinal direction. One end sides (right end in FIG. 6A and FIG. 6B) of the substrate 10, the adhesion layer 20A and the protection sheet 30A in the longitudinal direction are matched. The other end side (left end in FIG. 6A and FIG. 6B) of the protection sheet 30A in the longitudinal direction elongates from the other surface 10b side of the substrate 10 to pass through an end surface of the substrate 10 and bend toward the one surface 10a side of the substrate 10. Then, a part of the protection sheet 30A near the other end side is attached on the second surface 45b of the seal 45 through the adhesion layer 20B. The material and the thickness of the protection sheet 30A may be the same as those of the protection sheet 30, for example.

The protection sheet 30A is apart from the one surface 10a of the substrate 10 in FIG. 6B. However, not limited to this, and the protection sheet 30A may be provided to extend along the one surface 10a of the substrate 10, a side surface of the air cell 40 and the like through the adhesion layer 20B and another adhesion member.
(Method of Manufacturing Patch-Type Module of Second Embodiment)

Figure 7:
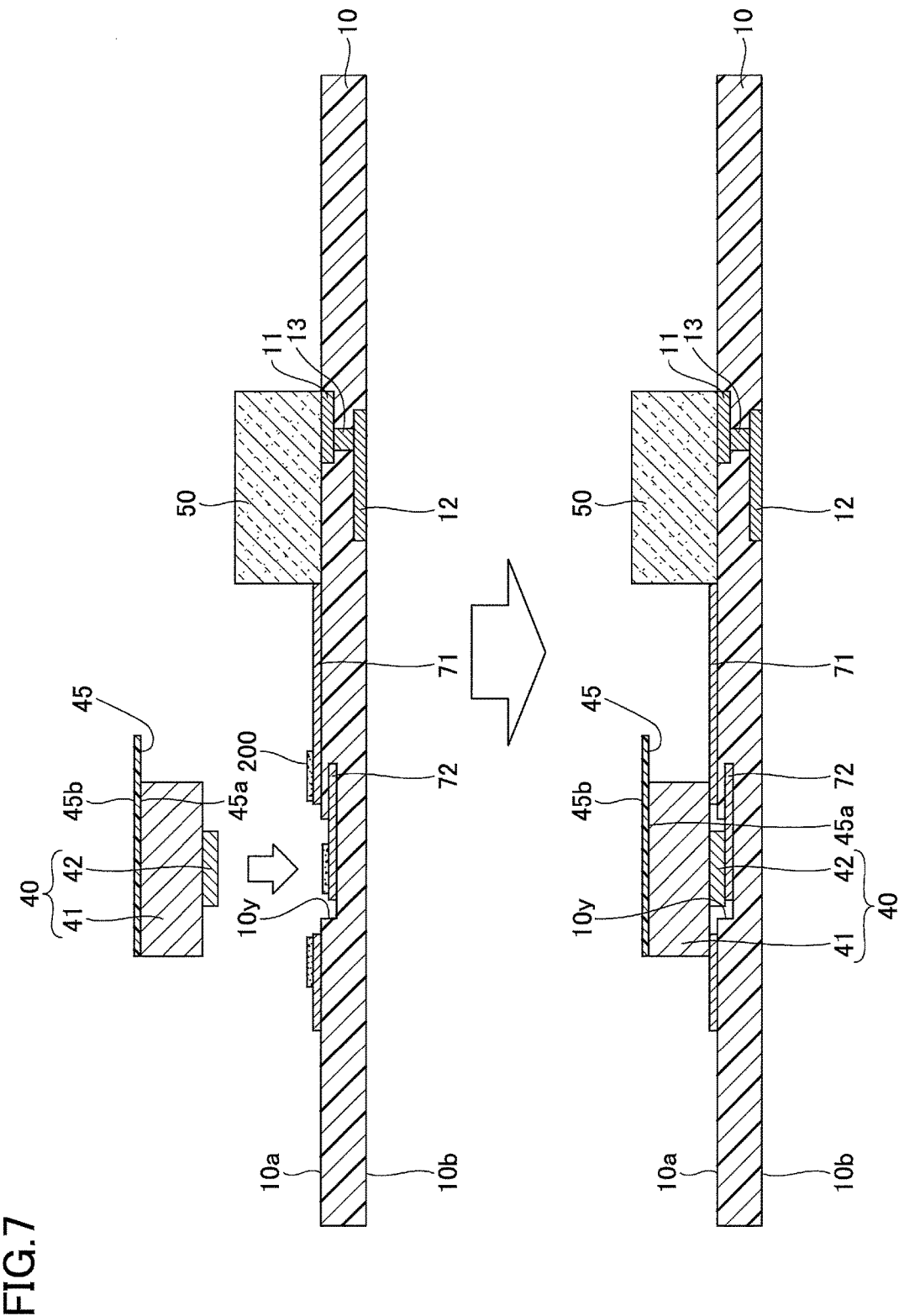
FIG. 7 is a cross-sectional view (No. 1) illustrating an example of a manufacturing step of the patch-type module of the second embodiment.
Figure 8A:
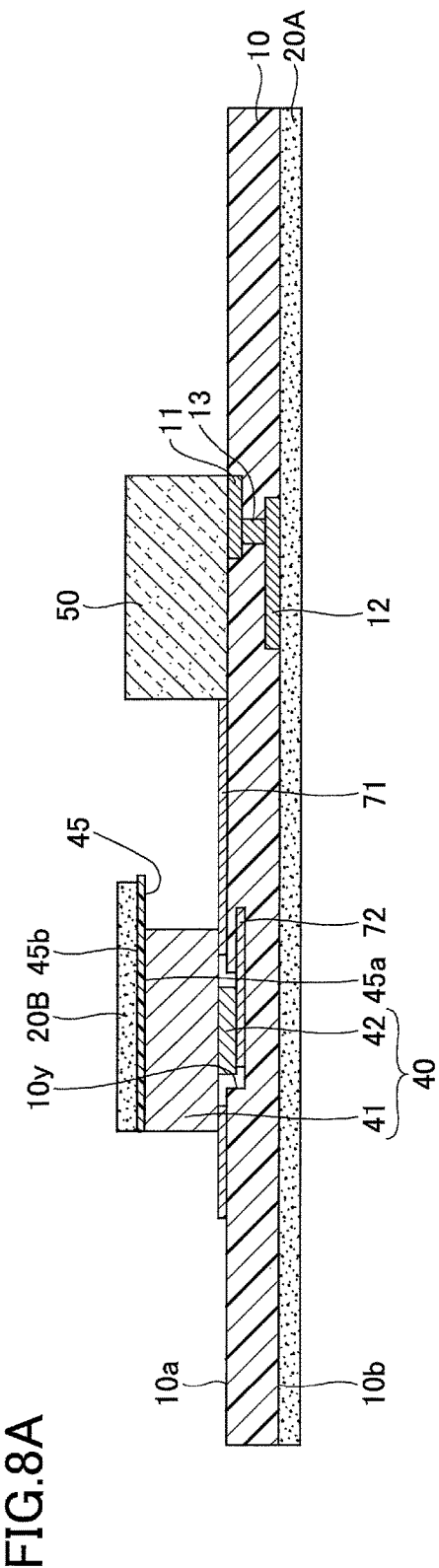
FIG. 8A and FIG. 8B are cross-sectional views (No. 2) illustrating an example of manufacturing steps of the patch-type module of the second embodiment.
Figure 8B:
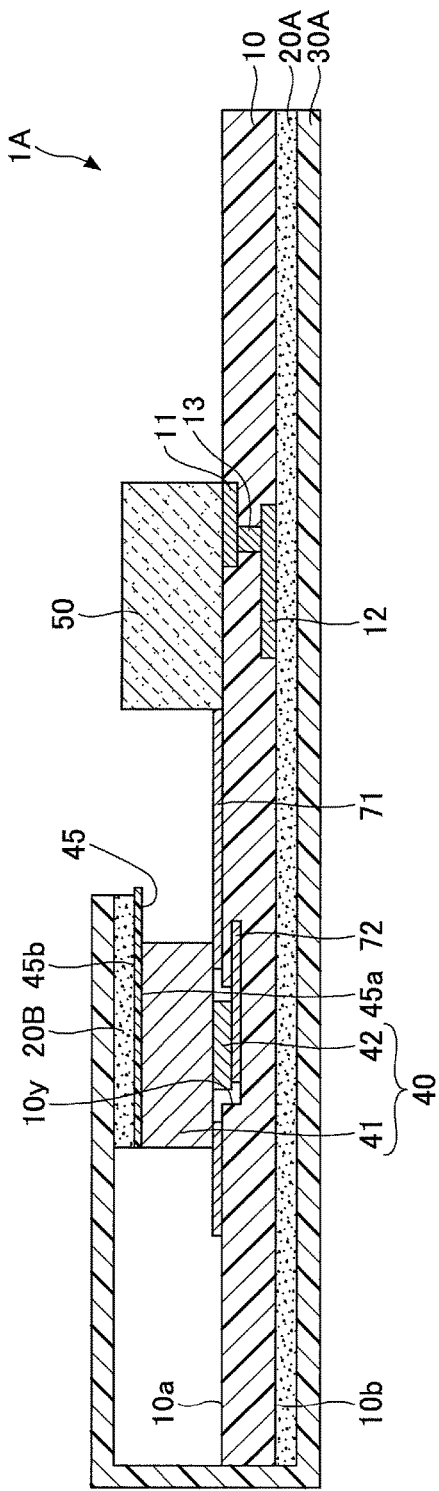

Next, a method of manufacturing the patch-type module 1A of the second embodiment is described. FIG. 7, FIG. 8A and FIG. 8B are cross-sectional views illustrating an example of manufacturing steps of the patch-type module 1A of the second embodiment.

First, in a step illustrated in FIG. 7, the concave portion 10y is formed at the one surface 10a of the substrate 10 by press working or the like. Then, after forming the wirings 71 and 72 at predetermined positions, respectively, by known plating, sputtering or the like, the electronic component 50 is mounted on the one surface 10a by reflowing or the like. Further, the conductive adhesive agent 200 such as a silver paste or the like is coated at predetermined positions of the wirings 71 and 72 at the upper surface side.

Next, the air cell 40, in which the seal 45 is attached to the back surface side, is mounted on the one surface 10a of the substrate 10 such that the negative electrode 42 is positioned at a lower side, and the conductive adhesive agent 200 is cured. With this, the main body 41 (positive electrode) of the air cell 40 is electrically connected to the wiring 71 via the conductive adhesive agent 200, and the negative electrode 42 is electrically connected to the wiring 72 through the conductive adhesive agent 200. This means that the air cell 40 is mounted on the one surface 10a side of the substrate 10 such that the first surface 45a of the seal 45 faces the one surface 10a of the substrate 10 while interposing the air cell 40 therebetween.

Next, in a step illustrated in FIG. 8A, the adhesion layer 20A is formed on the other surface 10b of the substrate 10 and the adhesion layer 20B is formed on the second surface 45b of the seal 45. The adhesion layers 20A and 20B may be formed by the same method as that for the adhesion layer 20, for example.

Next, in a step illustrated in FIG. 8B, after matching the positions of the one end sides (right side in FIG. 8B) of the adhesion layer 20A and the protection sheet 30A in the longitudinal direction, the protection sheet 30A is attached over the entirety of a lower surface of the adhesion layer 20A. Further, the other end side of the protection sheet 30A in the longitudinal direction that elongates from the other end side (left end in FIG. 8B) of the substrate 10 is bent from the other surface 10b side of the substrate 10 toward the one surface 10a side of the substrate 10 through the end surface of the substrate 10. Then, a part of the protection sheet 30A near the other end side is attached on the second surface 45b of the seal 45 through the adhesion layer 20B.

Here, materials or the like of the adhesion layer 20A and the protection sheet 30A are selected such that the adhesion strength between the adhesion layer 20A and the protection sheet 30A becomes greater than the adhesion strength between the adhesion layer 20A and the other surface 10b of the substrate 10. Further, materials or the like of the adhesion layer 20B, the protection sheet 30A, and the seal 45, are selected such that the adhesion strength between the adhesion layer 20B and the protection sheet 30A and the adhesion strength between the adhesion layer 20B and the seal 45 become greater than the adhesion strength between the seal 45 and the back surface of the main body 41 of the air cell 40.

With the above steps, the patch-type module 1A is completed. Here, steps to manufacture the single patch-type module 1A are described here. However, alternatively, a plurality of the patch-type modules 1A may be formed by using the substrate 10 in which a plurality or areas corresponding to the plurality of patch-type modules 1A, respectively, are aligned in a matrix form, and each of the patch-type modules 1A may be separated by press working or the like to obtain a plurality of the single patch-type module 1A.

Figure 9A:
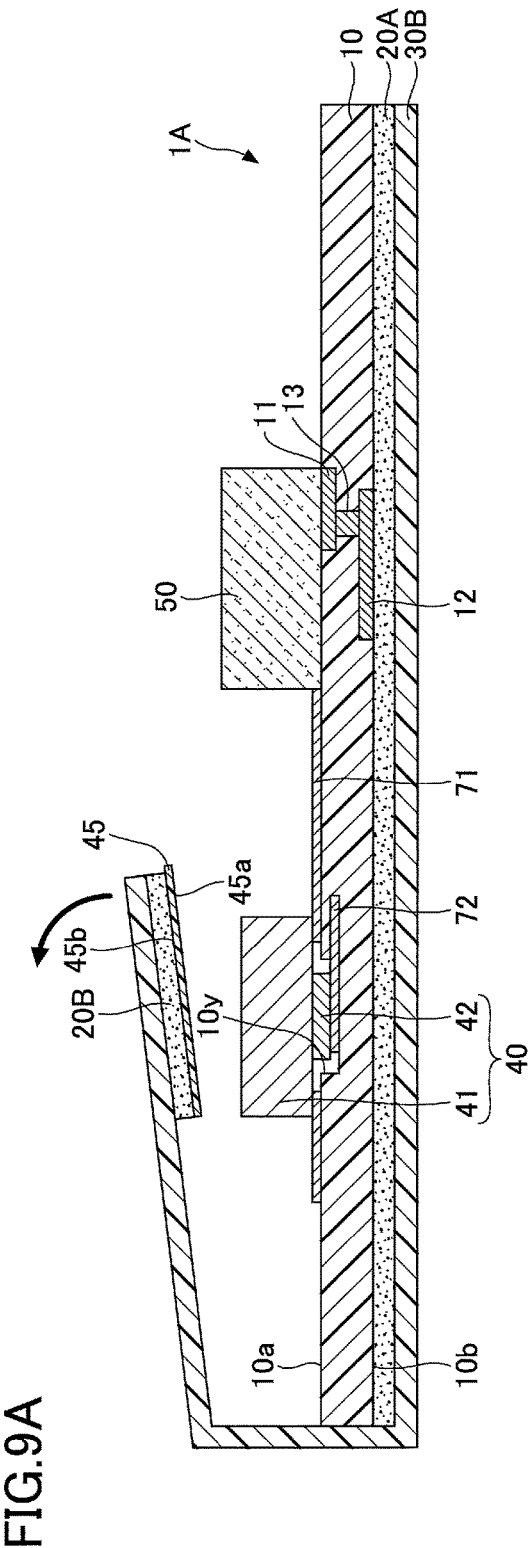
FIG. 9A and FIG. 9B are cross-sectional views for explaining how to use the patch-type module of the second embodiment.
Figure 9B:
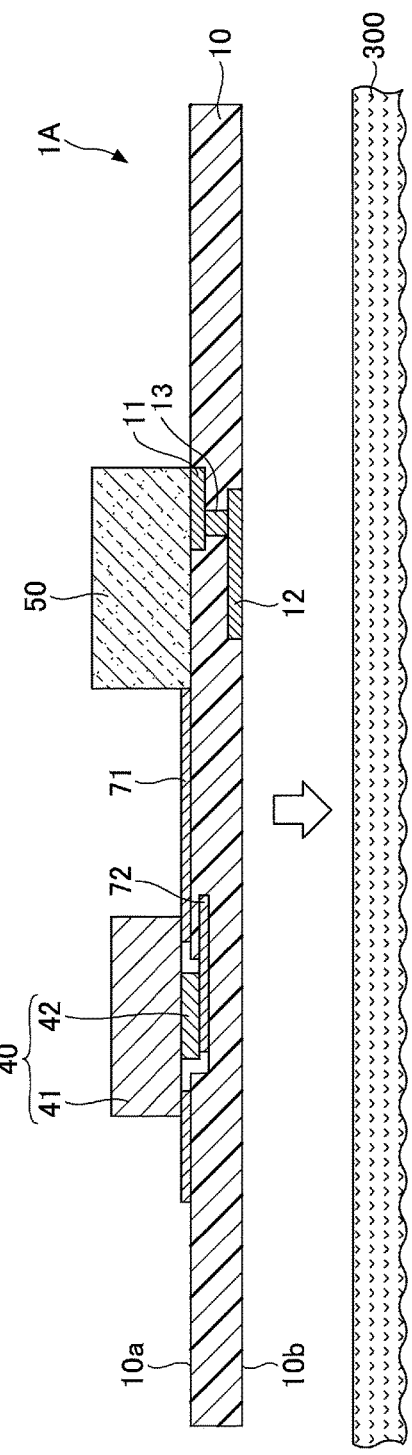

FIG. 9A and FIG. 9B are cross-sectional views for explaining how to use the patch-type module 1A of the second embodiment. When using the patch-type module 1A, first, as illustrated in FIG. 9A, the protection sheet 30A is peeled in a direction of an arrow.

As described above, the adhesion strength between the adhesion layer 20A and the protection sheet 30A is greater than the adhesion strength between the adhesion layer 20A and the other surface 10b of the substrate 10. Further, the adhesion strength between the adhesion layer 20B and the protection sheet 30A and the adhesion strength between the adhesion layer 20B and the seal 45 are greater than the adhesion strength between the seal 45 and the back surface of the main body 41 of the air cell 40.

Thus, when the protection sheet 30A is peeled in the direction of the arrow, first, the seal 45 is peeled from an interface between the back surface of the main body 41 of the air cell 40 with the protection sheet 30A and the adhesion layer 20B. When the protection sheet 30A is further peeled, the adhesion layer 20A is peeled from an interface between the other surface 10b of the substrate 10 with the protection sheet 30A. With this, introduction of air inside the air cell 40 is started and it is possible to supply electric power from the air cell 40 to the electronic component 50.

Next, as illustrated in FIG. 9B, the other surface 10b of the substrate 10 that has stickiness is attached on the target 300. With this, similar to FIG. 4B, predetermined data of the target 300 can be monitored using the patch-type module 1A.

Similar to the patch-type module 1 of the first embodiment, according to the patch-type module 1A of the second embodiment, as illustrated in FIG. 9A and FIG. 9B, the protection sheet 30A and the seal 45 are peeled at the same time by a single peeling operation, and usability is improved. In other words, as it is possible to start the operation of the air cell 40 and to expose the other surface 10b of the substrate 10, which is the sticky surface, by a single operation, usability is improved.

Further, as the air cell 40 is directly mounted on the one surface 10a of the substrate 10 by inserting the negative electrode 42 in the concave portion 10y provided in the substrate 10, it is unnecessary to use the cell holder 110. With this, similar to the patch-type module 1 of the first embodiment, the module can be obtained by a low cost and also is eco-friendly.

According to the embodiments, a patch-type module capable of starting an operation of a cell (air cell in this embodiment) and exposing a sticky surface by a single peeling operation can be provided.

Although a preferred embodiment of the patch-type module has been specifically illustrated and described, it is to be understood that minor modifications may be made therein without departing from the spirit and scope of the invention as defined by the claims.

The present invention is not limited to the specifically disclosed embodiments, and numerous variations and modifications may be made without departing from the spirit and scope of the present invention.

For example, various air cells having various structures may be used. For example, the plan shape of the air cell may not be a circular shape, and may be an ellipse shape, a rectangular shape or the like. Further, the main body of the air cell is not necessarily the positive electrode, and the positive electrode and the negative electrode may be provided at any desired positions of the main body.

Further, a plurality of the air cells may be mounted to the patch-type module.

Further, as the patch-type module of the invention has a structure capable of enabling peeling of a seal of an air cell and exposing of a sticky surface of a substrate by a single operation, the invention includes various structures including such technical ideas and is not limited to the structures exemplified in the first and second embodiments.

Further, the protection sheet 30 or 30A may be peeled from an opposite side from the arrow illustrated in FIG. 4A or FIG. 9A.

What is claimed is:
1. A patch-type module comprising:
    a substrate provided with one surface and another surface that is opposite to the one surface, the other surface being a sticky surface, the substrate having a hole formed therethrough;
    an air cell mounted to the substrate;
    a seal that blocks air from entering the air cell, the seal having a first surface that is attached to a surface of the air cell;
    an electronic component mounted on the substrate and configured to be operated by power supplied from the air cell;
    an adhesion layer provided to cover the sticky surface of the substrate and a second surface of the seal that is opposite to the first surface; and
    a protection sheet that is attached to the sticky surface of the substrate through the adhesion layer, and attached to the second surface of the seal through the adhesion layer,
    wherein the air cell is disposed in the hole of the substrate such that the surface of the air cell is flush with the sticky surface, and the first surface of the seal is attached to both the surface of the air cell and to the sticky surface while the second surface of the seal is attached to the protection sheet through the adhesion layer, wherein the adhesion strength between the adhesion layer and the protection sheet is greater than the adhesion strength between the adhesion layer and the sticky surface of the substrate, and wherein when the protection sheet is peeled, the adhesion layer and the seal are peeled together to expose the sticky surface of the substrate and start introduction of air inside the air cell so that electric power is capable of being power supplied to the electronic component from the air cell.

2. The patch-type module according to claim 1, wherein the substrate has flexibility and stretchability and is formed to have an elongated shape.

3. A patch-type module comprising:

a substrate provided with one surface and another surface that is opposite to the one surface, the other surface being a sticky surface, the substrate having a hole formed therethrough;

an air cell mounted to the substrate;

a seal that blocks air from entering the air cell, the seal having a first surface that is attached to a surface of the air cell;

an electronic component mounted on the substrate and configured to be operated by power supplied from the air cell;

an adhesion layer provided to cover the sticky surface of the substrate and a second surface of the seal that is opposite to the first surface; and a protection sheet that is attached to the sticky surface of the substrate through the adhesion layer, and attached to the second surface of the seal through the adhesion layer, wherein the air cell is disposed in the hole of the substrate such that the surface of the air cell is flush with the sticky surface, and the first surface of the seal is attached to both the surface of the air cell and to the sticky surface while the second surface of the seal is attached to the protection sheet through the adhesion layer, wherein each of the adhesion strength between the adhesion layer and the protection sheet and the adhesion strength between the adhesion layer and the seal is greater than the adhesion strength between the seal and the air cell, wherein the adhesion strength between the adhesion layer and the protection sheet is greater than the adhesion strength between the adhesion layer and the sticky surface of the substrate, and wherein when the protection sheet is peeled, the adhesion layer and the seal are peeled together to expose the sticky surface of the substrate and start introduction of air inside the air cell so that electric power is capable of being power supplied to the electronic component from the air cell.

4. The patch-type module according to claim 1, wherein the electronic component includes a sensor that obtains predetermined data from a target on which the patch-type module is stuck.

5. The patch-type module according to claim 4, wherein the electronic component includes at least one of a memory unit that stores the predetermined data and a radio transmitter that sends the predetermined data to an external device by radio communication.

6. A patch-type module comprising:

a substrate provided with one surface and another surface that is opposite to the one surface, the other surface being a sticky surface;

an air cell mounted to the substrate;

a seal that blocks air from entering the air cell, the seal having a first surface that is attached to the air cell;

an electronic component mounted on the substrate and configured to be operated by power supplied from the air cell;

an adhesion layer provided to cover the sticky surface of the substrate and a second surface of the seal that is opposite to the first surface; and a protection sheet that is attached to the sticky surface of the substrate through the adhesion layer, and attached to the second surface of the seal through the adhesion layer, wherein each of the adhesion strength between the adhesion layer and the protection sheet and the adhesion strength between the adhesion layer and the seal is greater than the adhesion strength between the seal and the air cell, wherein the adhesion strength between the adhesion layer and the protection sheet is greater than the adhesion strength between the adhesion layer and the sticky surface of the substrate, and wherein when the protection sheet is peeled, the adhesion layer and the seal are peeled together to expose the sticky surface of the substrate and start introduction of air inside the air cell so that electric power is capable of being power supplied to the electronic component from the air cell.

* * * * *